United States Patent [19]

Goodenough et al.

[11] Patent Number: 5,506,884
[45] Date of Patent: Apr. 9, 1996

[54] RADIATION PHANTOM AND TEST METHODS EMPLOYING THE SAME

[75] Inventors: David J. Goodenough, Myersville, Md.; Joshua R. Levy, Salem, N.Y.

[73] Assignee: Phantom Laboratory, Incorporated, Salem, N.Y.

[21] Appl. No.: 519,823

[22] Filed: Aug. 25, 1995

[51] Int. Cl.$^6$ ................................................ G01D 18/00
[52] U.S. Cl. ......................... 378/207; 378/18; 250/252.1
[58] Field of Search .................................... 378/204, 207, 378/19, 18; 250/252.1 R

[56] References Cited

U.S. PATENT DOCUMENTS

| | | | |
|---|---|---|---|
| 4,055,771 | 10/1977 | Goodenough et al. | 378/145 |
| 4,126,789 | 11/1978 | Vogl et al. | 378/145 |
| 4,233,507 | 11/1980 | Volz | 378/18 |
| 4,344,183 | 8/1982 | Jacobson | 378/207 |
| 4,460,832 | 7/1984 | Bigham | 250/505.1 |
| 4,527,057 | 7/1985 | Guyton et al. | 378/207 |
| 4,638,502 | 1/1987 | Yaffe | 378/207 |
| 4,794,631 | 12/1988 | Ridge | 378/207 |
| 4,843,619 | 6/1989 | Sheridan | 378/207 |
| 4,873,707 | 10/1989 | Robertson | 378/18 |
| 5,056,130 | 10/1991 | Engel | 378/207 |
| 5,095,499 | 3/1992 | Wentz | 378/207 |
| 5,187,731 | 2/1993 | Shimura | 378/207 |

*Primary Examiner*—Don Wong
*Attorney, Agent, or Firm*—Heslin & Rothenberg

[57] ABSTRACT

A radiation phantom comprising a solid opaque housing having an inner chamber is provided within which a test pattern for quantifying image quality, and at least one dosimeter for simultaneously measuring radiation dosage are randomly disposed. A tamper proof means is connected to the opaque housing such that the test pattern and the at least one dosimeter are unviewable and unaccessible within the chamber. Thus, the test pattern and the at least one dosimeter are "interlocked" within the radiation phantom housing such that the radiation phantom can be employed to accurately evaluate off-site a radiation machine's imaging of the radiation phantom without requiring the presence of an independent qualified technician on-site during irradiation of the phantom.

17 Claims, 6 Drawing Sheets

RADIATION PHANTOM AND TEST METHODS EMPLOYING THE SAME

FIELD OF THE INVENTION

The present invention relates in general to radiation machine calibration devices and methods, and more particularly, to an improved radiation phantom and test method employing the same to objectively evaluate off-site an x-ray machine without requiring on-site presence of an independent technician during imaging of the radiation phantom.

BACKGROUND ART

X-ray phantoms are known calibration devices and teaching aids for conventional x-ray machines. Prior art phantoms are available in a number of variations, some being plastic replicas of the human body or specific portions thereof, while others consist of actual human bones cast in plastic. These phantoms are used to train x-ray technicians in the proper positioning of the human body for the various x-ray images that are taken for diagnosis, and the resulting films may be studied to aid in calibrating an x-ray machine for identifying the radiographic image of known structures.

Extensive scientific work has been done in measuring x-ray dose and image quality of x-ray imaging equipment. Test phantoms and measurements have evolved to facilitate evaluation of an x-ray imaging machine. From a regulatory point of view, radiation dose is often the key parameter of concern. Today, the general policy is to protect patients from unreasonable radiation dose, while still allowing the radiologist to obtain an image of acceptable quality. Some imaging facilities have adopted their own rigorous quality assurance programs, while others have not.

In recent years, there has been increased interest in independent, third party monitoring of image quality along with radiation dose. A variety of phantoms and dosimeters have been used for this type of application. Image quality can often be increased by utilizing protocols resulting in excessive radiation dose levels, while dose measurements can be minimized by selecting protocols which provide inadequate x-ray images. For this reason, accurate testing has traditionally required an on-site visit by an independent technician or scientist who is able to verify that the same protocols are followed for both the image quality and radiation dose measurements.

A significant disadvantage of this monitoring approach is the cost associated with having an independent technician or scientist accompany the phantom to oversee the imaging thereof. With ever increasing concern for the quality of care, there is increased interest in regulatory evaluation of x-ray equipment. However, this runs counter to the pressure on governmental agencies to reduce costs. Thus, a genuine need exists in the art for facilitating gathering of reliable, non-falsifiable radiation dose and image quality information by an independent agency without the presence of their own independent technician or scientist on-site to oversee performance of the measurements.

DISCLOSURE OF INVENTION

Briefly summarized, the present invention comprises in one aspect a radiation phantom which includes an opaque housing having a chamber therein. A test pattern comprising at least one test object, for use in quantifying image quality, and at least one dosimeter, for simultaneously measuring radiation dosage, are randomly disposed within the housing's chamber. A tamper resistant sealing means is connected to the housing such that the test pattern and the dosimeter are unaccessible and thereby interlocked in an unviewable arrangement within the phantom. Because of this interlocking, the radiation phantom can be used by an independent agency to accurately evaluate off-site a radiation machine without requiring the on-site presence of its technician during the imaging of the phantom.

In another aspect, a method is presented for employing the above-summarized radiation phantom. This method includes: using the radiation machine to produce an x-ray image of the radiation phantom; and thereafter, removing the at least one dosimeter from the phantom, and reading the at least one dosimeter to obtain a measurement of radiation dosage and reading the x-ray image to obtain an evaluation of image quality produced by the radiation machine. The removal of the dosimeter, which may comprise destroying a tamper resistant seal, is preferably performed by an independent testing agency. If desired, the on-site radiologist may be required to initially read the x-ray image and forward such readings to the independent testing agency for evaluation of the radiologist's interpretative skills.

To restate, provided herein is a radiation phantom which enables measurements of image quality and radiation dose of an x-ray machine or scanner without an on-site visit by an independent technician trained in the skill of image quality and dose evaluation. The radiation phantom design is unique in that image quality and dose tests are randomly disposed in an unpredictable arrangement in the same phantom such that the measurements are "interlocked" within the imaging field. Because radiation dose and image quality are so interrelated, the x-ray machine can not be set to improve one measurement without degrading the other. Through this interlocking of image quality and radiation dose measurements, any tampering can be quickly identified by evaluation of both the dose and image quality data. The ability to verify measurement quality based on the simultaneously collected dose and image information enables accurate off-site evaluation of imaging equipment without requiring an independent technician on-site to observe the measurements.

The radiation phantom presented herein will have great value to independent test agencies which are responsible for evaluating equipment disposed over a wide geographic area. This phantom can be shipped from the test agency to the different sites for on-site technicians to irradiate and image the phantom. The images, dosimeters, and on-site radiologists' findings can then be returned to the test agency. This would significantly reduce the time and expense associated with traditional on-site audits. In many instances, the radiation phantom presented herein will enable testing of radiation machines where on-site testing would not be cost-feasible.

BRIEF DESCRIPTION OF THE DRAWINGS

These and other objects, advantages and features of the present invention will be more readily understood from the following detailed description of certain preferred embodiments of the invention, when considered in conjunction with the accompanying drawings in which.

BEST MODE FOR CARRYING OUT THE INVENTION

A significant aspect of a radiation phantom design in accordance with this invention is the simultaneous measurement of dose and image quality performance using randomly disposed tests in a tamper proof design. Because dose and image quality tests are unpredictably "interlocked" in a single phantom, an on-site radiologist can not change dose to improve image quality or degrade image quality to reduce dose.

Figure 1:
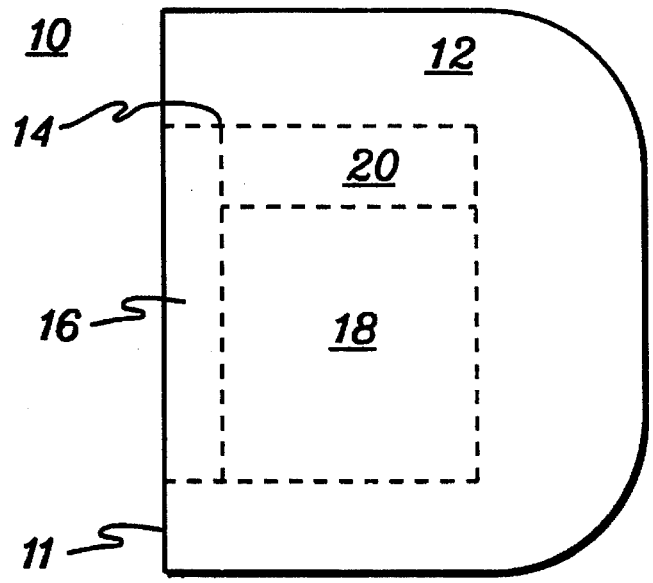
FIG. 1 is an elevational view of a radiation phantom in accordance with the present invention.
Figure 1A:
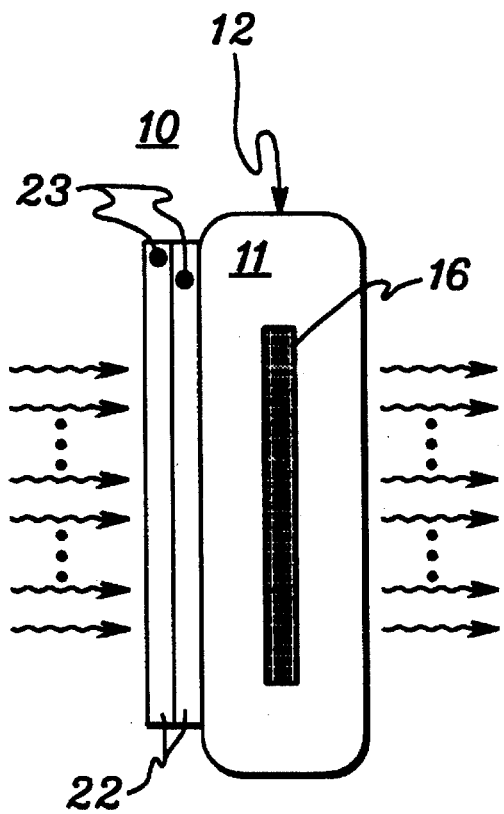
FIG. 1a is an edge view of the radiation phantom of FIG. 1.

FIGS. 1 & 1a depict one embodiment of a radiation phantom, generally denoted 10, in accordance with this invention. Phantom 10 comprises a solid, opaque material fabricated, for example, from any of the "tissue simulating materials" known in the art. The material is selected to simulate an appropriate parameter of the tissue intended to be imaged by the radiation machine. In other words, the characteristics of the phantom are the analog of a body to be imaged onto film or an electronic detection array. The phantom allows for an equivalent absorption in an analogous manner to the way the body would absorb the x-rays. Obviously, the materials selected to accomplish this will vary based upon whether the absorptive characteristics of bone material or tissue material are to be copied.

Defined within an opaque body or housing 12 of phantom 10 is an inner chamber 14 (shown in phantom) within which resides an insert structure 16 inserted into chamber 14 through an opening in an edge surface of housing 12 (see FIG. 1a). Insert structure 16 contains a test pattern 18 and room for a multichip dosimeter insert 20. The specific locations for the multichip dosimeter and the test pattern can vary depending upon established scientific location protocols, design efficiency and the desirability of random arrangements. Significant to this invention, however, is that phantom 10 holds both the dosimeters and the test pattern within the inner chamber in an unviewable and unpredictable arrangement. This is facilitated by fabricating insert structure 16 of an opaque material such that when inserted within the phantom body, the locations of the dosimeters and the test pattern are unviewable from the opening in the housing edge 11 through which the insert structure is inserted.

Also significant to note is that the dosimeters and the test pattern are "interlocked" within the radiation phantom so that the image quality measurement is "locked" with the dose measurement. This is because the random nature of placement and the opaque nature of the phantom make it impossible for an on-site radiologist to know or predict the location of these two tests within the phantom, and therefore one test can not be exposed without exposing the other test. Such simultaneous measurements assure that there is no undetected change in dose to improve image quality or degradation of image quality to reduce dose.

One or more layers of attenuation structures 22 (FIG. 1a) can be affixed to body 12 so as to reside between a source of radiation of an imaging machine under test and the inner chamber of phantom housing 12 containing the randomly located test pattern and dosimeter(s). Each attenuation structure 22 could comprise a thin filament of different density or different thicknesses of radiation absorbing material. These attenuation structures may or may not be included with the phantom based upon design and material considerations. Internal indicia 23 are provided in each attenuation structure 22 for inclusion in the radiation image in order that a reviewing technician is aware of the type and number of attenuation structures employed with the radiation phantom 10. Use of the attenuation structures 22 will allow the radiation phantom to evaluate equipment performance for different sized patients.

Figure 2:
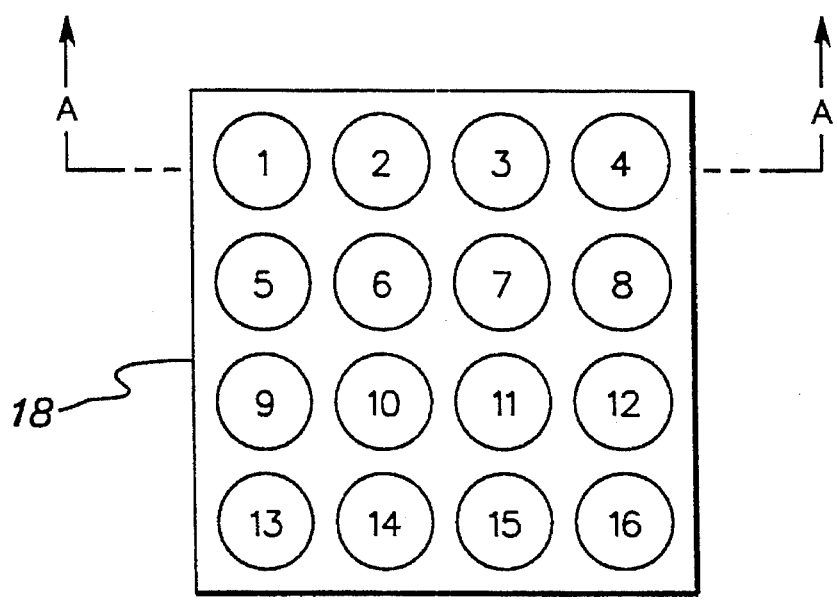
FIG. 2 is an elevational view of one embodiment of a test pattern for a radiation phantom in accordance with the present invention, wherein the test pattern comprises an array of test objects.

One embodiment of test pattern 18, depicted in FIG. 2, comprises a 4×4 array containing 16 test locations (labeled "1, 2, . . . 16"), each of which may contain a test object. The specific test objects employed within test pattern 18 may comprise any one of a variety of objects known in the art which when irradiated are useful for characterizing image quality of a radiation machine. Preferably, the objects within test pattern 18 are randomly disposed among the individual test locations. This random disposition of test objects can be used to test an on-site radiologist's ability to read the resultant radiation image.

Figure 3A:
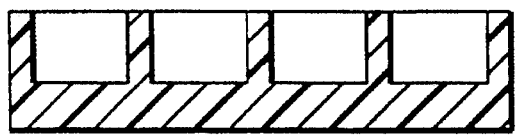
FIGS. 3a–3c are cross-sectional views of FIG. 2 taken along lines A—A during one fabrication embodiment of the test pattern.
Figure 3B:
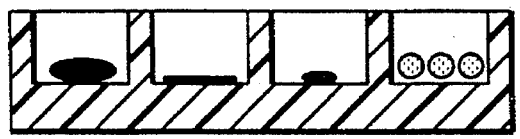
Figure 3C:
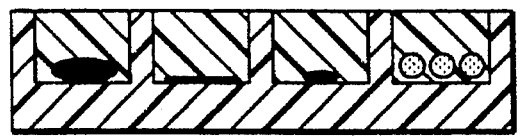

FIGS. 3a–3c sequentially depict cross-sections of structures obtained during fabrication of test pattern 18. In FIG. 3a, the test pattern is initially fabricated with a desired number of test locations, i.e., four locations in this cross-sectional view. Within each test location may be placed a test object (FIG. 3b) which may vary based on size, shape, quantity and/or material of fabrication. Finally, the test objects are encapsulated (FIG. 3c) within the respective test locations, thereby defining the test pattern generally depicted in FIG. 2. Again, this pattern is by way of example only and those skilled in the art will recognize that a wide variety of different test patterns may be employed. For example, one or more test objects may comprise various sized nylon fibers that simulate fibrous structures, different sized abrasive grains may be used to simulate microcalcifications, disks of various diameter and thickness may simulate tumor-like masses, or some of the test locations may simply be left blank.

Figure 4A:
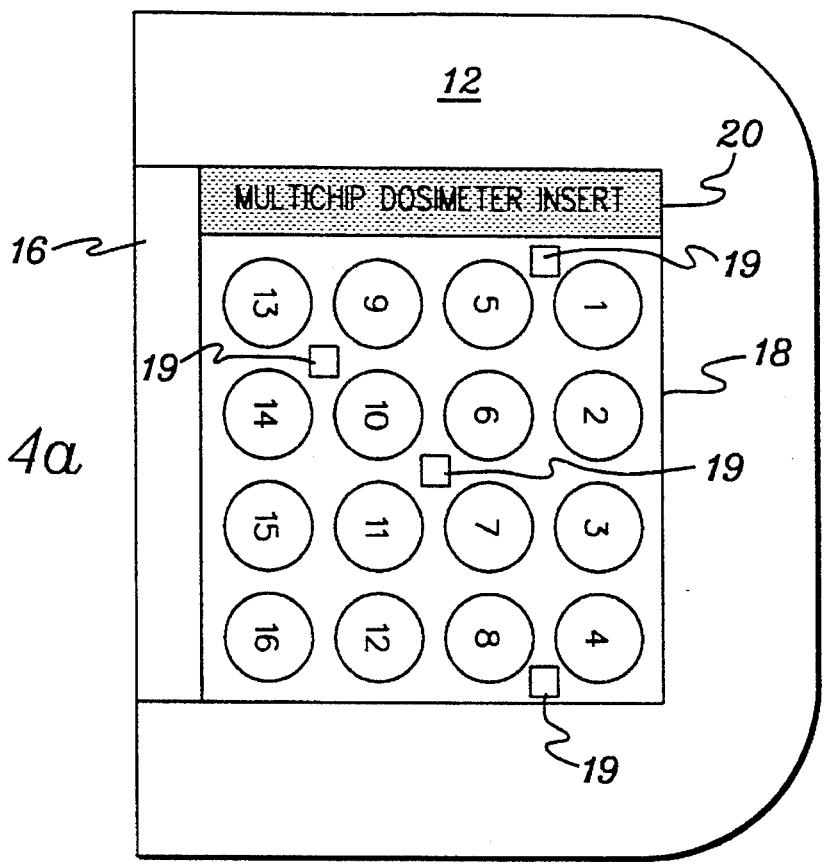
FIGS. 4a–4d are elevational views of alternative embodiments for placement of the test pattern and a multichip dosimeter insert within the chamber.
Figure 4B:
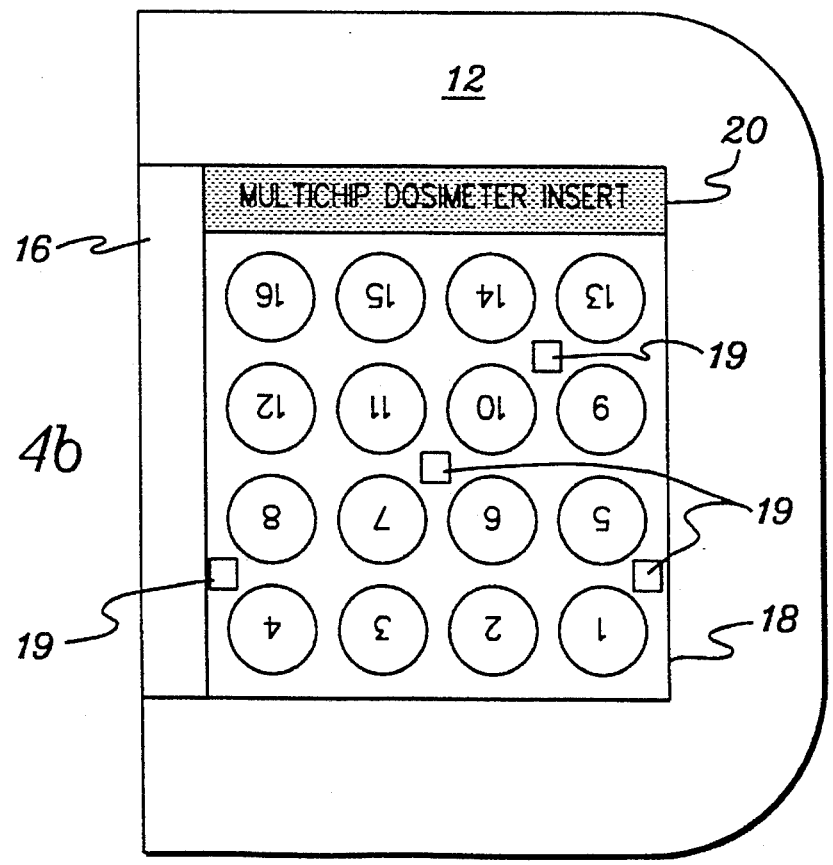
Figure 4C:
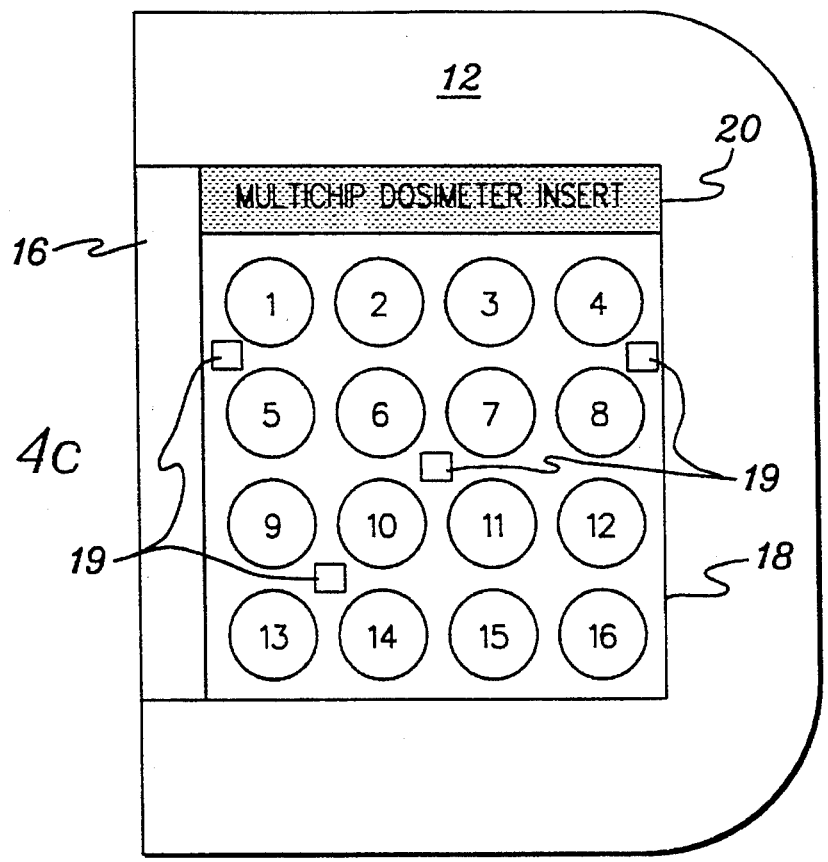
Figure 4D:
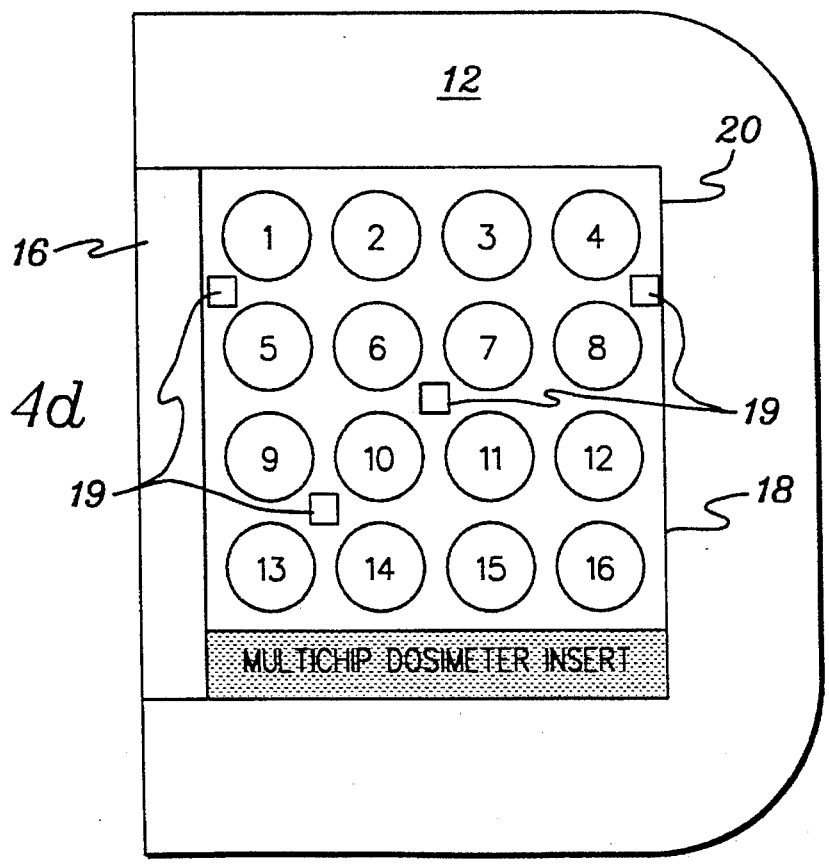
Figure 5A:
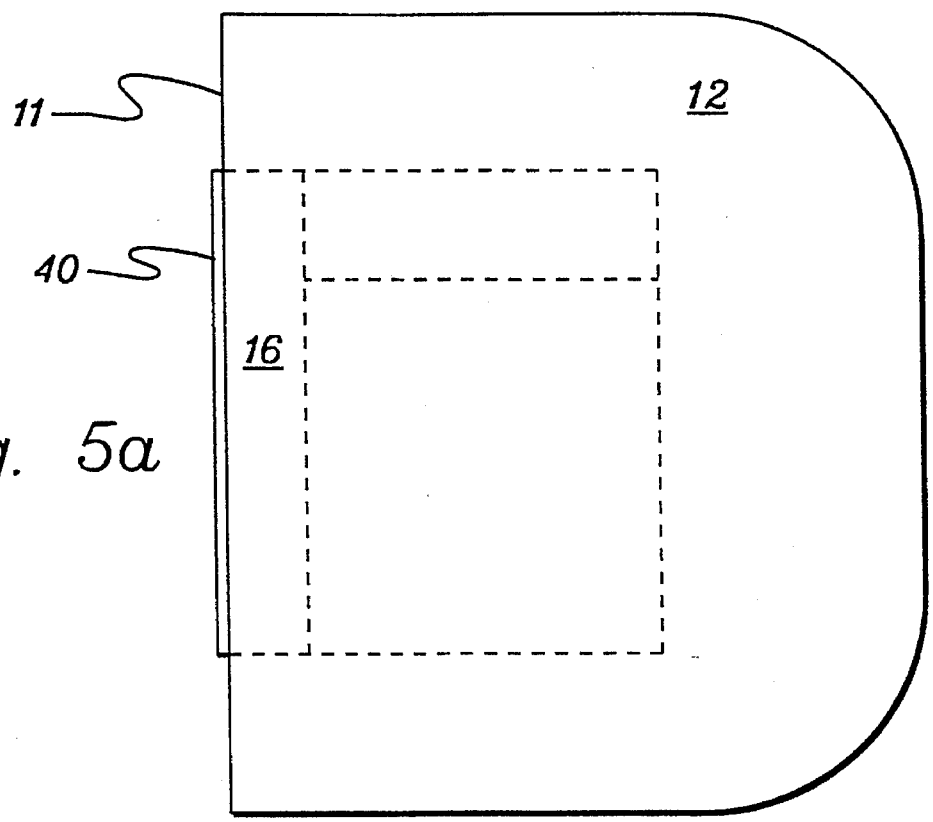
FIG. 5a & 5b are an elevational view and an edge view, respectively, of the radiation phantom in accordance with the present invention showing use of a tamper resistant adhesive seal over an access opening to the chamber.
Figure 5B:
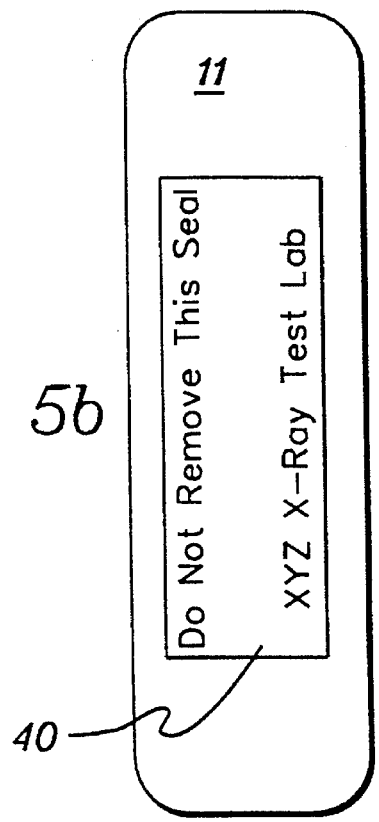

Further, as shown in FIGS. 4a–4d the orientation of the test pattern within the inner chamber of the phantom may vary. In FIG. 4a, the test pattern is oriented sideways within the insert structure, in FIG. 4b the test pattern is held upside down within the insert structure, in FIG. 4c the test pattern is held upright within the insert structure, and in FIG. 4d the locations of the test pattern and the multichip dosimeter insert are varied. These four orientations and/or dispositions are provided by way of example only. Those skilled in the art will recognize that there are a large variety of possible orientations and pattern arrangements which could be employed to accomplish randomness of the test objects within the phantom to eliminate the possibility of on-site predictability. Further, a variety of insert structures could be devised, each of which would be designed to hold a differently configured test pattern 18 within the inner chamber of the radiation phantom. The manufacturer would simply determine which particular insert structure is to be employed at any given time.

Interspersed among the randomly placed test objects in the 16 test locations are multiple dosimeters 19, that could comprise transluminesence-type dosimeters which are known in the art. Additional commercially available dose inserts could also be sealed into the phantom housing. For example, a multichip dosimeter insert 20 such as that available from Landauer Inc. of Glenwood, Ill. may be employed. The ability to locate the various dosimeters at various positions within the inner chamber prevents an on-site radiologist from knowing or predicting the locations of the dosimeters and thereby shielding that particular location(s) in a manner which would reduce dose readings. Again, the number and location(s) of dosimeters depicted herein are by way of example only.

Once the test components have been assembled within the insert structure 16 and placed within the inner chamber of the radiation phantom, a tamper proof adhesive seal 40 is preferably affixed over the opening in edge surface 11 to the inner chamber. The size and location of the tamper proof seal will depend upon the design of the radiation phantom. For example, if the phantom is designed in a clamshell configuration, then a seal which affixes to both the upper and lower halves of the clamshell phantom would be sufficient. In the design presented herein, the insert structure 16 is assumed to comprise an opaque material such that seal 40 may or may not be transparent.

There are wide variety of options available for insuring tamper resistance of the radiation phantom. In addition to an adhesive label with destruction cuts, the phantom could be vacuumed wrapped with an identifiable material so that any deterioration of the wrapping would indicate that the phantom has been tampered with and nullify the test. Alternatively, any mechanical locking mechanism could be used.

Figure 6:
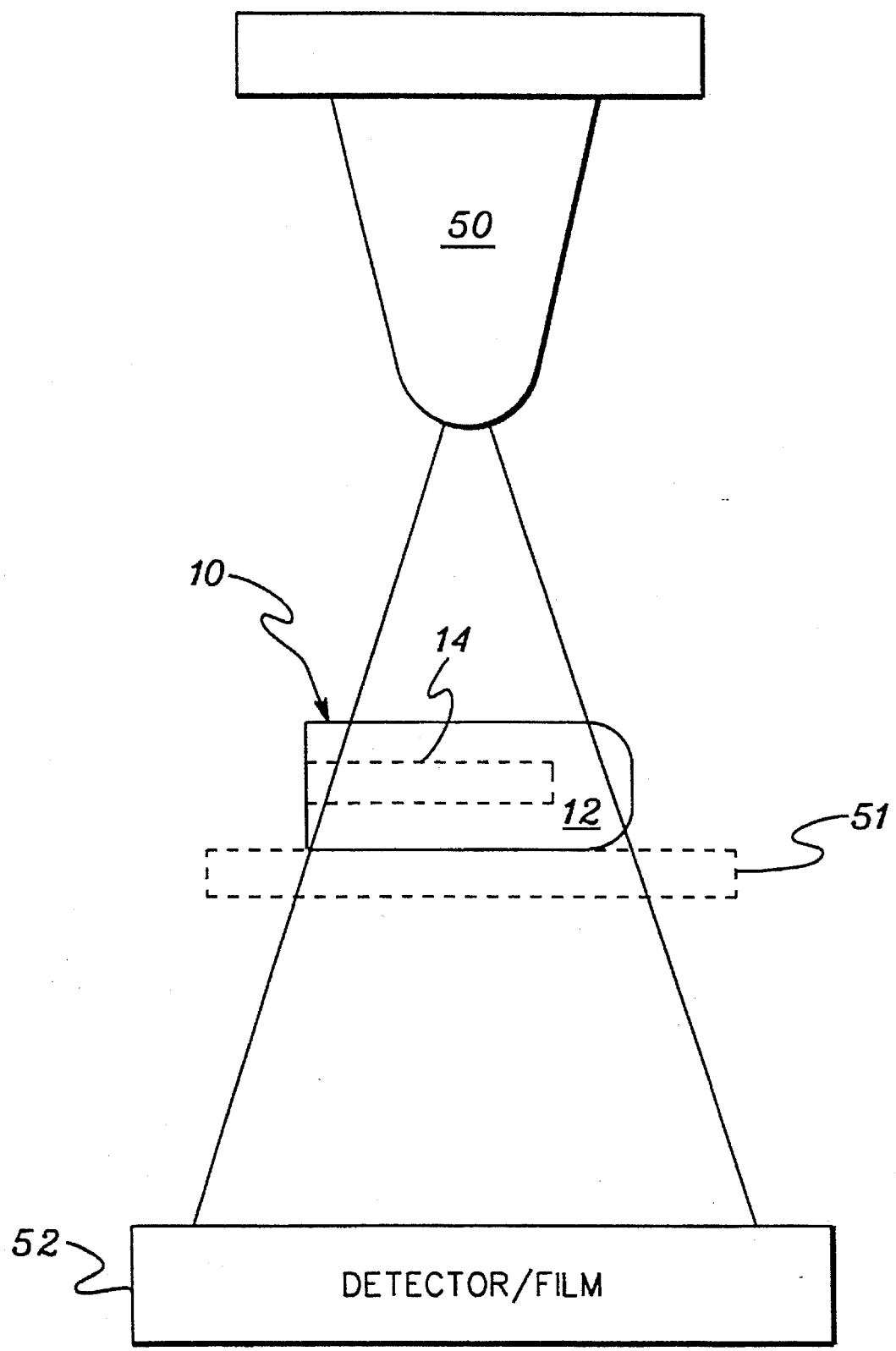
FIG. 6 is a simplified schematic showing disposition of the radiation phantom within a radiation imaging machine such that a radiation image of the phantom is exposed onto a detector or film for purposes of evaluation.

FIG. 6 depicts use of the radiation phantom 10 within a radiation machine 50. Machine 50 emits x-ray radiation from a general point source (not shown). The x-rays are directed at the radiation phantom 10 which is disposed on a table 51 such that inner chamber 14 of phantom body 12 is imaged onto a detection mechanism such as a TV camera, film camera or conventional x-ray film. In this arrangement, and attenuation structures (not shown) would be disposed atop the phantom body 12. This figure is a simplified depiction of a radiation machine and is provided herein for completeness only. More detailed discussion of radiation machines can be found in the literature.

A radiation phantom in accordance with this invention will have different possible applications for remote quality and dose monitoring which will affect the configuration. For example, if equipment only is to be evaluated, then an unknown, fixed test pattern and dosimeter insert could be employed. With such a structure, the on-site radiologist would image the phantom following specific protocols and then return the phantom to the independent test agency with the radiation image, for example, recorded on film. If the radiologist's ability to read the radiation image is also to be evaluated, then a test pattern with random test objects would be used. This particular phantom would again be imaged by the on-site radiologist following specific protocols, after which the radiologist would read the image to characterize the particular objects capable of being identified. The phantom, film and radiologist's notes would then be returned to the independent test agency for evaluation.

A basic test sequence would thus be as follows:

1. An independent test lab or agency would insert fresh dosimeters and a test pattern into the insert structure which would then be placed within the inner chamber of the radiation phantom. The lab employee would note the position of the inserts and the orientation of the random test objects. A tamper proof seal would there after be affixed over the opening to the inner chamber of the phantom.

2. The phantom would be forwarded to a hospital or other imaging facility.

3. At the imaging facility, the radiologist would irradiate and image the phantom using predefined patient protocols or specified protocols for the anatomy and patient size which the phantom represents. The film or other images of the radiation phantom are then developed or otherwise recorded.

4. Optionally, the on-site radiologist reviews the radiation image and indicates all identifiable test objects.

5. The phantom, radiation image, and radiologist's notes are returned to the test agency.

6. At the test agency, the phantom is checked to ensure there has been no tampering, the seal is broken and the dosimeter(s) is removed.

7. The dosimeter(s) is read and the phantom images are evaluated for image quality.

8. Thereafter, the independent agency can assemble an accurate report on the radiation machine's dose and image quality, as well as the radiologist's reading thereof.

From the above-discussion, those skilled in the art will note that provided herein is a radiation phantom which enables measurements of image quality and radiation dose of an x-ray machine or scanner without an on-site visit by an independent technician trained in the skill of image quality and dose evaluation. The radiation phantom design is unique in that image quality and dose tests are randomly disposed in an unpredictable arrangement in the same phantom such that the measurements are "interlocked" within the imaging field. Because radiation dose and image quality are so interrelated, the x-ray machine can not be set to improve one measurement without degrading the other. Through this interlocking of image quality and radiation dose measurements, any tampering can be quickly identified by evaluation of both the dose and image quality data. The ability to verify measurement quality based on the simultaneously collected dose and image information enables accurate off-site evaluation of imaging equipment without requiring an independent technician on site to observe the measurements.

The radiation phantom presented herein will have great value to independent test agencies which are responsible for evaluating equipment disposed over a wide geographic area. This phantom can be shipped from the test agency to the different sites, for on-site technicians to irradiate and image the phantom. The images, dosimeters, and on-site radiologists' findings can then be returned to the test agency. This would significantly reduce the time and expense consumed in on-site audits. In many instances, the radiation phantom presented herein will enable testing of radiation machines where on-site testing would not be cost-feasible.

While the invention has been described in detail herein in accordance with certain preferred embodiments thereof, many modifications and changes therein may be effected by those skilled in the art. Accordingly, it is intended by the appended claims to cover all such modifications and changes as fall within the true spirit and scope of the invention.

We claim:

1. A radiation phantom comprising:

an opaque housing having a chamber therein;

a test pattern comprising at least one test object for quantifying image quality, and at least one dosimeter for simultaneously measuring radiation dosage, said at least one test object of said test pattern and said at least one dosimeter being randomly disposed within said chamber of said opaque housing; and a tamper resistant sealing means connected affixed to said opaque housing wherein said test pattern and said at least one dosimeter are unaccessible and thereby interlocked in an unviewable arrangement within said opaque housing, whereby said radiation phantom can be used to accurately evaluate off-site a radiation machine's imaging of the radiation phantom.

2. The radiation phantom of claim 1, wherein said chamber comprises an accessible chamber, and wherein said tamper resistant sealing means comprises an adhesive seal affixed to said opaque housing so as to prevent access to said accessible chamber without destruction of said adhesive seal.

3. The radiation phantom of claim 1, wherein said opaque housing includes an opening to said chamber, and wherein said tamper resistant sealing means comprises a seal which is opaque and affixed to said opaque housing over said opening such that access to said chamber requires destruction of said seal.

4. The radiation phantom of claim 1, wherein said at least one test object of said test pattern comprises multiple test objects, and wherein said at least one dosimeter is randomly disposed among said multiple test objects.

5. The radiation phantom of claim 1, wherein said radiation machine comprises an x-ray imaging machine.

6. The radiation phantom of claim 1, further comprising at least one attenuation structure affixed to said opaque housing, said at least one attenuation structure allowing said radiation phantom to mimic at least one additional phantom structure such that said radiation machine can be evaluated for said at least one additional phantom structure.

7. The radiation phantom of claim 6, wherein said at least one attenuation structure comprises multiple layers of attenuation structures affixed to said opaque housing, wherein when said radiation phantom is imaged said multiple layers of attenuation structures are disposed between a source of radiation of the radiation machine and the chamber containing the randomly disposed at least one test object and at least one dosimeter, each attenuation structure of said multiple layers of attenuation structures including an internal marker.

8. The radiation phantom of claim 1, wherein said at least one dosimeter comprises multiple dosimeters, and wherein said multiple dosimeters and said at least one test object are randomly disposed within said chamber in said opaque housing.

9. The radiation phantom of claim 1, wherein said at least one test object comprises an array of test objects positioned on an insert structure, and wherein said at least one dosimeter comprises multiple dosimeters, said multiple dosimeters being randomly placed among said array of test objects on said insert structure, said insert structure being disposed within said chamber of said opaque housing.

10. The radiation phantom of claim 9, wherein at least some dosimeters of said multiple dosimeters comprise transluminescense dosimeters.

11. The radiation phantom of claim 10, wherein said insert structure is positionable within said chamber with said test pattern in a variety of orientations.

12. The radiation phantom of claim 10, wherein said multiple dosimeters include a prepackaged multichip dosimeter disposed adjacent to said array of test objects.

13. The radiation phantom of claim 1, wherein said opaque housing comprises a solid, tissue simulating material.

14. A method for using a radiation phantom comprising:
an opaque housing having a chamber therein;
a test pattern comprising at least one test object for quantifying image quality, and at least one dosimeter for simultaneously measuring radiation dosage, said at least one test object of said test pattern and said at least one dosimeter being randomly disposed within said chamber of said opaque housing; and a tamper resistant sealing means connected affixed to said opaque housing wherein said test pattern and said at least one dosimeter are unaccessible and thereby interlocked in an unviewable arrangement within said opaque housing, whereby said radiation phantom can be used to accurately evaluate off-site radiation machine's imaging of the radiation phantom;

said method comprising the steps of:
(a) employing the radiation machine to produce an image of the radiation phantom; and
(b) subsequent to said step (a), removing the at least one dosimeter from the opaque housing an reading the at least one dosimeter and the image to evaluate radiation dose and image quality of the radiation machine.

15. The method of claim 14, wherein said step (b) comprises performing said removing and said reading off-site from said radiation machine by an independent testing agency.

16. The method of claim 15, further comprising prior to said step (b), requiring a radiologist working on-site with the radiation machine to initially evaluate the image, said initial evaluation also being forwarded to said independent testing agency for accuracy confirmation.

17. The method of claim 15, wherein said removing of said step (b) includes unlocking the tamper resistant sealing means.

\* \* \* \* \*